United States Patent [19]

Feld

[11] Patent Number: 5,274,093

[45] Date of Patent: Dec. 28, 1993

[54] PROCESS FOR THE PREPARATION OF SODIUM THIOBARBITURATE

[75] Inventor: Marcel Feld, Cologne, Fed. Rep. of Germany

[73] Assignee: Huels Aktiengesellschaft, Marl, Fed. Rep. of Germany

[21] Appl. No.: 930,307

[22] Filed: Aug. 13, 1992

Related U.S. Application Data

[63] Continuation-in-part of Ser. No. 769,152, Sep. 27, 1991, abandoned, which is a continuation of Ser. No. 560,049, Jul. 30, 1990, abandoned.

[30] Foreign Application Priority Data

Aug. 3, 1989 [DE] Fed. Rep. of Germany ....... 3925689

[51] Int. Cl.$^5$ .......................................... C07D 239/02
[52] U.S. Cl. .................................................. 544/299
[58] Field of Search ........................................ 544/299

[56] References Cited

U.S. PATENT DOCUMENTS

| | | |
|---|---|---|
| 782,740 | 2/1905 | Fischer ................. 544/299 |
| 814,496 | 3/1906 | Wolfes ................. 544/299 |
| 893,308 | 7/1908 | Conrad ................. 544/299 |
| 1,038,101 | 9/1912 | Engelmann ........... 544/299 |
| 1,038,102 | 9/1912 | Engelmann ........... 544/299 |
| 1,739,662 | 12/1924 | Boedecker ........... 544/299 |
| 1,954,429 | 4/1934 | Shonle ................. 544/299 |
| 1,998,101 | 4/1935 | Shonle ................. 544/299 |
| 2,051,846 | 8/1936 | Halbig et al. ........ 544/299 |
| 2,161,212 | 6/1939 | Whitmore et al. ... 544/299 |
| 2,876,225 | 3/1959 | Donnison ............. 544/299 |

FOREIGN PATENT DOCUMENTS 411277 8/1991 European Pat. Off. .
770344 3/1957 United Kingdom .

OTHER PUBLICATIONS

Koppel et al J. Org. Chem. 26 (1961) 792.
L. N. Goldyre, et al. Chem. Abst. 48, 4531e (1953).
"Beilstein Handbuch der Organischen Chemie" vol. 24, 1936, Springer Verlag. Seite 476, Absatz 2.
Jaromir Kavalek et al. Collection of Czechoslovak Chem. Commu. vol. 45, 1980, p. 734.

Primary Examiner—Cecilia Tsang
Attorney, Agent, or Firm—Felfe & Lynch

[57] ABSTRACT

Sodium thiobarbiturate is prepared by reacting dimethyl malonate, thiourea and sodium methylate in methanol as the solvent at elevated temperatures, preferably at reflux temperature under atmospheric pressure.

3 Claims, No Drawings

PROCESS FOR THE PREPARATION OF SODIUM THIOBARBITURATE

This is a continuation-in-part of copending U.S. patent application Ser. No. 07/769,152, filed Sep. 27, 1991 now abandoned; which is a continuation of U.S. patent application Ser. No. 07/560,049, filed Jul. 30, 1990, now abandoned.

FIELD OF THE INVENTION

The present invention relates to a novel industrial process for the preparation of the sodium salt of thiobarbituric acid, which can be converted into the free thiobarbituric acid by treatment with a mineral acid. Thiobarbituric acid and its sodium salt are useful, inter alia, as intermediates for the preparation of insecticides or pesticides.

The process of the present invention is based on the reaction of dimethyl malonate with approximately equimolar amounts each of thiourea and sodium methylate in methanol as the solvent at elevated temperatures, preferably at reflux temperature, under atmospheric pressure.

BACKGROUND OF THE INVENTION

It is known from the literature (J. pr. Chem 35, 456; J. Org. Chem. 26, (1961) 792) that sodium thiobarbiturate and in turn thiobarbituric acid can be prepared by reacting thiourea with a sodium salt of diethyl malonate in an ethanolic medium, but the yield of thiobarbituric acid is an unsatisfactory 84% of theory. It is also known that thiobarbituric acid can be prepared by starting from thiourea, diethyl malonate and an alkali metal alcoholate. Depending upon the alkali metal alcoholate which is used, this process produces different yields, that is, 60% when sodium ethylate is used and as little as 37% of theory when the less expensive sodium methylate is used (Sbornik Statei Obshchei Khim. 2, 1273-4 (1953)). In addition to the entirely unsatisfactorily yields, such a process also has the disadvantage that it results in ethanol/methanol mixtures which require an additional step in the product isolation procedure.

OBJECT OF THE INVENTION

It is an object of the present invention to prepare sodium thiobarbiturate with high yields by means of an industrially simple process using inexpensive sodium methylate.

Other objects and advantages of the process of the present invention will become apparent as the description thereof proceeds.

DESCRIPTION OF THE INVENTION

We have discovered that, contrary to the teachings of the literature, it is possible to prepare sodium thiobarbiturate with high yields by means of an industrially simple process which comprises reacting thiourea, dimethyl malonate and sodium methylate in methanolic solution.

Thus, the present invention relates to a process for the preparation of sodium thiobarbiturate in which the three starting materials are provided in an approximately molar ratio of 1:1:1. Excesses of up to 100 mol%, particularly up to 25 mol%, of the reactants are possible but without any particular advantage. The reaction is performed at elevated temperatures, preferably at 40 to 120° C., especially under reflux conditions of methanol, and under atmospheric pressure.

In a preferred embodiment, all or at least most of the methanolic filtrate which is obtained by conventional solid/liquid separation after the reaction is complete and the target product has been isolated, is used over again as a reaction medium for further reactions of dimethyl malonate with thiourea and sodium methylate.

In the process of the present invention, the amount of methanol which is used as the reaction medium can be varied within wide limits. However, with a view toward optimum utilization of the technical equipment, a relatively small amount of solvent is preferred. Hence, it is advantageous to use 2 to 4 parts by weight of methanol per part by weight of thiourea. A portion of the methanol can be used in this process in the form of a methanolic sodium methylate solution.

The sequence in which the starting materials dimethyl malonate, thiourea and sodium methylate are added, is not of significant importance. However, in the performance of the process on an industrial scale it may be of practical advantage to initially introduce the solid thiourea in the form of a solution in methanol, and to add to this solution, either in succession or simultaneously, the malonic ester and a methanolic sodium methylate solution. Alternatively, one or two of the three components can be added batchwise or continuously when the reaction conditions are established.

A high yield of the target product is achieved even when the starting materials are employed in equimolar ratios in the process of the instant invention. In the case of sodium methylate, however, an excess can be advantageous if the sodium thiobarbiturate is not to be processed further into thiobarbituric acid, but is to be methylated, for example, to form 2-(methylthio)barbituric acid. Since thiobarbituric acid acts as a polybasic acid with respect to sodium methylate, an excess of the base also forms a disodium salt of thiobarbituric acid which, for example, produces dialkylated products in alkylation processes.

For the purpose of working up the reaction mixture resulting from the process pursuant to the instant invention, the sodium thiobarbiturate product which is sparingly soluble in methanol is isolated by means of a conventional solid/liquid separation procedure and, if appropriate, is washed with methanol. All or some of the filtrate, optionally after having been concentrated to a desired volume, can be used over again several times as a reaction medium for further reactions. This repeated recycling of the methanolic mother liquor not only drastically reduces the amounts of solvent or residues generated by the reaction, which have to be worked up or disposed of, but also leads to a significant improvement of the total yield to more than 99%, and at the same time to surprisingly high purities in the range of 99.8 to 99.9%.

When the methanolic mother liquor and the washing filtrate are recycled, they can also be concentrated by distilling off the methanol as late as during the reaction. This procedure makes it possible to compensate in a convenient manner for the increased amount of methanol compared with the preceding batch, on the one hand by the preceding condensation reaction and the washing methanol, and, is appropriate as the solvent for sodium methylate, and thus provide constant and identical concentration ratios in the reaction mixture to be worked up.

The following examples illustrate the present invention and will enable others skilled in the art to understand it more completely. It should be understood, however, that the invention is not limited solely to the particular examples given below.

EXAMPLE 1

A solution of 150.7 g (2.0 mols) of thiourea and 237.8 g (1.8 mols) of dimethyl malonate in 400 g of methanol was refluxed, and a solution of 97 g (1.8 mols) of $NaOCH_3$ in 224 g of methanol was added over the course of 15 minutes. After the mixture had been refluxed for 4 more hours, it was cooled to room temperature and filtered, and the filter cake was washed with 100 g of methanol and then dried. The yield was 278 g (93% of theory based on the amount of malonic ester) of sodium thiobarbiturate in the form of white crystals of 99.8% purity.

The methanol filtrates were concentrated to 400 g, 137 g (1.8 mols) of thiourea and 237.8 g (1.8 mols) of dimethyl malonate were first added to the concentrate, and later, under reflux conditions a solution of 97 g (1.8 mols) of sodium methylate in 224 g of methanol was added, and the resulting mixture was processed further in the manner described above. In the same manner, each of the methanolic filtrates which had been concentrated to 400 g were employed two additional times in the reaction of 137 g of dimethyl malonate and 97 g of sodium methylate. The total yield from all four runs was 1185 g (99.1% of theory) of sodium thiobarbiturate with a purity of 99.8 to 99.9%.

EXAMPLE 2

Example 1 was repeated, and both thiourea and sodium methylate were initially introduced in methanolic solution or in solution in the methanolic filtrate of the preceding experiment which had been concentrated to 400 g, and were then added to the malonic ester under reflux conditions. The initial run of the test series yielded 283.1 g (94.7% of theory) of sodium thiobarbiturate. The total yield from all four runs was 1187 g (99.2% of theory) of sodium thiobarbiturate with a purity of 99.8 to 99.9%.

EXAMPLE 3

Example 1 was repeated, and both the malonic ester and the sodium methylate were initially introduced in methanolic solution or in solution in the methanolic filtrate from a preceding run which had been concentrated to 400 g; thiourea was added in portions over the course of 45 minutes at 60° C., and the above described procedure was followed. The yield from the initial run was 274.1 g (91.7% of theory) of sodium thiobarbiturate, and the total yield from all four runs was 1182 g (98.9% of theory) of sodium thiobarbiturate with a purity of 99.7 to 99.9%.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

I claim:

1. The method of preparing sodium thiobarbiturate with a yield of more than 99% of theory and a purity of at least 99.8%, which comprises reacting dimethyl malonate, thiourea and sodium methylate in methanol at the reflux temperature of methanol at atmospheric pressure, at a mol ratio of 1 mol of one of the three reactants thiourea, dimethyl malonate and sodium methylate per 1 to 1.25 mols of the other two reactants, separating the sodium thiobarbiturate from the methanol by a conventional solid/liquid separation procedure, and recycling all or some of the methanol recovered in the solid/liquid separation procedure for use as a reaction medium in a subsequent reaction of thiourea, dimethyl malonate and sodium methylate to form sodium thiobarbiturate.

2. The method of claim 1, wherein the methanol recovered in the solid/liquid separation procedure is concentrated to a lesser volume prior to being recycled.

3. The method of claim 1, wherein methanol is used as the reaction medium in an amount of 2 to 4 parts by weight per 1 part by weight of thiourea.

* * * * *